United States Patent [19]

Oehler

[11] 4,445,860
[45] May 1, 1984

[54] RECHARGEABLE FLUID DRIVEN DENTAL TOOL

[76] Inventor: John H. Oehler, R.R. 15, Box 409, Brazil, Ind. 47834

[21] Appl. No.: 378,886

[22] Filed: May 17, 1982

[51] Int. Cl.³ ............................................. A61C 1/05
[52] U.S. Cl. ................................................... 433/132
[58] Field of Search ............... 433/132; 415/502, 503; 60/671, 651

[56] References Cited

U.S. PATENT DOCUMENTS

| | | | |
|---|---|---|---|
| 2,871,562 | 2/1959 | Kern | 433/132 |
| 3,589,126 | 4/1969 | Zotto | 60/671 |
| 3,987,633 | 10/1976 | Ford | 60/671 |
| 4,092,830 | 6/1978 | Rilett | 60/671 |

*Primary Examiner*—Robert Peshock
*Attorney, Agent, or Firm*—Woodward, Weikart, Emhardt & Naughton

[57] ABSTRACT

A rechargeable fluid driven dental tool. A hand piece includes a hollow handle forming a container chargeable with a liquefied gas. A rotatable turbine mounted in the head of the tool is connected by means of a passage to the container of liquefied gas. A control valve extending into the passage controls the amount of gas flow to the turbine with a pressure relief valve limiting maximum liquid flow and allowing the liquefied gas to change to gas for driving the turbine.

1 Claim, 2 Drawing Figures

RECHARGEABLE FLUID DRIVEN DENTAL TOOL

BACKGROUND OF THE INVENTION

This invention is in the field of hand held drills and more specifically dental tools. Dental drills are driven either by a belt pulley combination or by means of pressurized fluid directed against a rotatably mounted turbine having the dental tool mounted thereon. In either case, the hand piece must be connected to a remote source of energy either by flexible conduits having the pressurized fluid therein or by belts. Another approach is to rotate the drill by means of a miniature motor mounted in the head of the hand piece with the motor then being connected by wires to a remote source of electrical energy. An example of an air driven motor located in the hand piece is shown in U.S. Pat. No. 4,040,311 and Re. 28,649. An earlier version is shown in U.S. Pat. No. 77,370 wherein the air motor is driven by compressed air operated by a foot-bellows.

Modern dental hand pieces rotate the dental drill at speeds in excess of 250,000 rpm. As a result, the source of driving energy is located remotely from the hand piece particularly since the hand piece must be very compact and easy and convenient for a dentist to manipulate. On the other hand, the various connections required between the dental hand piece and the remote source of energy limits the freedom of movement of the dentist while also necessitating various hoses, wires or belts in the area of the patient's mouth. These problems have been solved by the design of the dental hand piece disclosed herein which has a rechargeable self-contained energy source. Through the utilization of an expansion chamber and constrictor, a charge of pressurized liquid is contained within the handle of the hand piece with the liquid then changing to a pressurized gas for driving the tool providing a very efficient source of energy.

SUMMARY OF THE INVENTION

One embodiment of the present invention is a rechargeable fluid driven tool comprising a main body including a handle, shank and head connected together with the handle being hollow defining a storage container to hold fluid at a first pressure, the shank including passage means leading from the container to the head, externally operable control means mounted to the main body and extending into the passage operable to control fluid flow therethrough and further operable to reduce the first pressure to a lower pressure, inlet valve means mounted to the main body and in fluid communication with the container being operable to allow fluid flow into the container to recharge same to the first pressure when connected to a remote supply of pressurized fluid and, rotable drive means mounted within the head and having an output drive shaft extending outwardly of the main body, the drive means positioned adjacent the passage means to receive fluid flowing therethrough rotating the drive means and the shaft when the inlet valve means is disconnected from the remote supply.

A further embodiment of the present invention is a dental hand piece with a self-contained energy source comprising: a main body with a hollow handle forming a rechargeable container to hold pressurized liquid, a head attached to the handle and a passage leading from the container to the head, the main body including an expansion chamber to allow the liquid from the container to expand to a gas, a turbine mounted in the head next to the passage to receive gas therefrom with means extending outwardly from the turbine to mountingly receive a dental tool, and, control means projecting into the main body to control fluid flow from the container to the turbine.

It is an object of the present invention to provide a dental hand piece having a rechargeable self-contained source of driving energy.

A further object of the present invention is to provide a portable tool having a rechargeable container of pressurized liquid provided thereon to drive the tool.

Related objects and advantages of the present invention will be apparent from the following description.

DESCRIPTION OF THE PREFERRED EMBODIMENT

Figure 1:
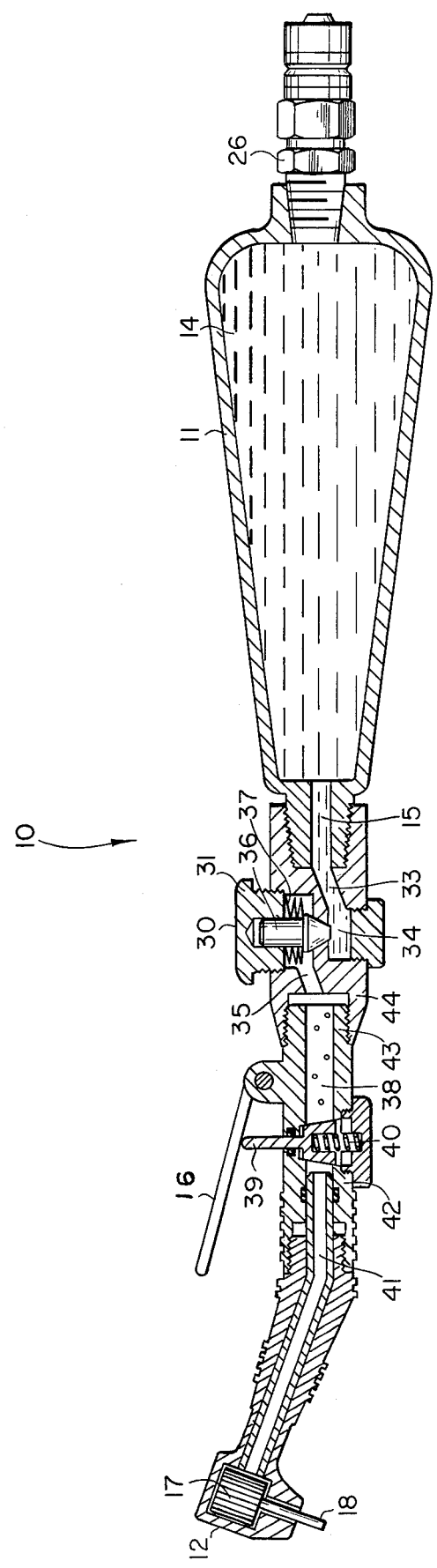
FIG. 1 is a cross-sectional view of a dental hand piece incorporating the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown a dental hand piece 10 having a main body with a handle 11 joined to the head 12 of the tool by means of a shank. The main body may be produced of various metal components assembled into a single main body. It is important that handle 11 be of sufficient strength to form a container 14 of pressurized liquid. A passage 15 leads from container 14 to pressure relief valve 30. The pressurized liquid changes state to gas in valve 30 prior to passing through control valve 34 and impinging upon and driving turbine 17 rotatably mounted within head 12. A rotatable drive shaft 18 is mounted to turbine 17 and extends outwardly from head 12 to mountingly receive a dental drill tool.

Figure 2:
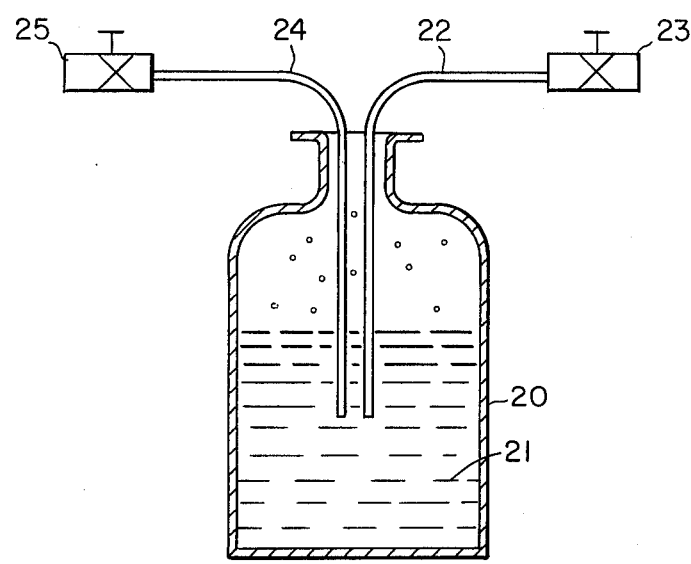
FIG. 2 is a fragmentary cross-sectional view of a source of pressurized liquid to recharge the tool of FIG. 1.

Located remotely from tool 10 is a tank 20 (FIG. 2) of pressurized liquid 21 with a first conduit 22 and associated valve 23 extending through the neck of the tank to facilitate filling of the tank. A second conduit 24 and associated valve 25 extends outwardly from the tank to enable the dentist to recharge tool 10. A conventional needle valve 26 is mounted to one end of handle 11 opening into container 14. Needle valve 26 mates with valve 25 enabling the pressurized liquid 21 to flow through conduit 24 until container 14 is charged to the pressure existing within tank 10. While a variety of inert liquefied gases may be provided to drive turbine 17, it is anticipated best results will be obtained by utilizing liquefied carbon dioxide at a pressure within tank 20 of approximately 56.5 atmospheres. Container 14 when initially charged will hold the liquefied carbon dioxide at a pressure of 56.5 atmospheres with the pressure slowly decreasing as the liquid is used to drive turbine 17. The tool is operable when disconnected from tank 20 as the pressure within container 14 lowers from the initial charging pressure of 56.5 atmospheres to a lower pressure.

A variable or rheostat control lever 16 is pivotally mounted to main body 11 and extends against control valve 39 mounted at location 42 of shank portion 43 allowing the operator to control the amount of gas passing from passage 38. Valve 39 extends into passage 38 and is operable to sealingly control gas flow therein as the pressure within container 14 reduces from the initial charging level to the lowest operable level. Spring 40 urges valve 39 to the normally closed position.

The shank of the handpiece includes two shank portions 43 and 44 threadedly connected together and to the handle of main body 11. Passage 15 leads to passage 33 formed in shank portion 44 which in turn leads to passage 34 formed in pressure relief valve 30. A second passage 35 in shank portion 44 leads to passage 34 but fluid flow therebetween is controlled and restricted by needle valve 36 providing a constriction means slidably mounted to head 31 threadedly mounted to shank portion 44. Spring 37 urges valve 36 downwardly to prevent fluid flow between passages 34 and 35; however, head 31 may be rotated upwardly to reduce pressure from spring 36 allowing liquid from passage 34 to move to passage 35 and in the process change state from a liquid to a gas. The pressure within passage 34 is approximately 830 lb/in$^2$ whereas the pressure in passage 35 is approximately 30 lb/in$^2$. Passage 35 leads to passage 38 and then to passage 41. Valve 36 limits maximum fluid flow into passage 35 with valve 39 fully opened thereby providing constant pressure to turbine 17 until pressure within container 14 drops to a certain level. In other words, pressure within container 14 is great enough to cause a constant maximum fluid flow through valve 30 when valve 39 is fully opened until the pressure within container 14 drops to a specified level.

All of the fluid within passage 41 is in gas form prior to contacting the turbine. The inert liquid within container 14 is at a pressure in excess of 50 atmospheres with the container being sized to hold in excess of four liquid ounces of carbon dioxide when full. In one embodiment, container 14 is approximately five inches in length holding five liquid ounces of carbon dioxide at a pressure of 56.5 atmospheres. As the liquid expands within passage 35 to a pressure of approximately 2 atmospheres, a very small amount of liquid flow from passage 34 will achieve a turbine speed in excess of 200,000 per minute. The tool is therefore very efficient utilizing a small amount of liquid from container 14 to drive the turbine. In the same embodiment, five liquid ounces within container 14 is sufficient to drive turbine 17 for a duration of approximately 8 minutes. Carbon dioxide is particularly useful with the dental hand piece shown in FIG. 1 since the inert liquefied gas will not change state to a gas at room temperature under the indicated pressures. A cutting surface may be provided directly onto the distal end of shaft 18 or the distal end may be threaded or otherwise provided with means to mountingly receive a tool having a cutting or polishing surface thereon. The dental hand piece shown in FIG. 1 is operable to rotate shaft 18 by fluid from container 14 when the tool is disconnected from tank 20 and not connected to any external source of energy. The indicated revolutions per minute of turbine 17 of 250,000 is achieved when container 14 is pressurized at 56.5 atmospheres. Valve 28 is mounted to the end of the handle and is in fluid communication with container 14 to provide for automatic release of pressure in the event the tool is accidentally pressurized in excess of a predetermined safety amount.

Many variations of the present invention are contemplated and included herein. For example, the tool shown in FIG. 1 may be used for purposes in addition to a dental tool. Further, additional fluid lines and passages may be provided in tool 10 to direct water or other washing mediums to a location adjacent shaft 18.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A dental hand piece including self-contained energy source comprising:
   a main body with a hollow handle forming a rechargeable container to hold pressurized liquid, a head attached to said handle and a passage leading from said container to said head, said main body including an expansion chamber to allow said liquid from said container to expand to a gas;
   a turbine mounted in said head next to said passage to receive gas therefrom with means extending outwardly from said turbine to mountingly receive a dental tool;
   finger push lever means mounted to said main body and extendable into said passage to control the amount of fluid flow from said container to said turbine; and,
   externally operable needle valve means mounted to said main body and extending into said passage means controllably allowing liquid within said container to expand to a gas as said liquid flows into said passage.

* * * * *